United States Patent
Clark, Jr.

Patent Number: 5,094,230
Date of Patent: Mar. 10, 1992

[54] METHOD AND APPARATUS FOR TREATING PEYRONIE'S DISEASE

[76] Inventor: Buford E. Clark, Jr., 307 S. Grove Rd., Richardson, Tex. 75081

[21] Appl. No.: 762,415

[22] Filed: Sep. 19, 1991

[51] Int. Cl.$^5$ .............................................. A61F 5/41
[52] U.S. Cl. ..................................................... 600/38
[58] Field of Search ............................... 128/79, 38, 40

[56] References Cited

U.S. PATENT DOCUMENTS

| | | | |
|---|---|---|---|
| 3,744,486 | 7/1973 | Wilson | 128/79 |
| 4,175,554 | 11/1979 | Gerow | 128/79 |
| 4,641,638 | 2/1987 | Perry | 128/79 |
| 4,718,411 | 1/1988 | Stewart | 128/79 |
| 4,741,329 | 5/1988 | Marcune | 128/79 |

Primary Examiner—Cary E. O'Connor
Attorney, Agent, or Firm—Ross, Howison, Clapp & Korn

[57] ABSTRACT

A method for treating Peyronie's disease includes providing an elongated tube having an inner diameter that is substantially equal to the outer diameter of an erect penis, such that the walls thereof will be adjacent the outer surface of the erect penis. A base portion is provided on the end of the elongated tube that is operable to be disposed about the base portion of an adult male penis to provide a seal therewith to air flow. The adult male penis is inserted into the end of the tube having the base portion associated therewith and the base portion moved downward against the base of the penis. A high air flow vacuum source is disposed and connected to the opposite end of the tube, such that a negative pressure is formed therein. The negative pressure results in the penis moving from a flaccid condition to an erect condition. After the penis has become erect, the seal between the base portion and the base of the penis is broken and made numerous times to create a turbulent air flow upward along the inner sides of the tube between the interior of the inner sides of the tube and the outer surface of the penis. This turbulent flow creates a significant amount of agitation within the tissue of the corpus cavernosum of the penis, as the tube is moved from side-to-side and in all directions.

4 Claims, 1 Drawing Sheet

METHOD AND APPARATUS FOR TREATING PEYRONIE'S DISEASE

TECHNICAL FIELD OF THE INVENTION

The present invention pertains in general to therapeutic devices for treating Peyronie's Disease, and more particularly, to an apparatus for creating turbulence in the cavernous sheath of the penis to achieve the therapeutic affect.

BACKGROUND OF THE INVENTION

Peyronie's Disease consists of a dysplasia of the cavernous sheath of the penis consisting of a fibrous thickening and contracture of the investing facia of a corpora, not unlike Dupuytren's contracture. The general cause of this disease is unknown. However, it primarily occurs in adult males, and the contracture usually results in deviation of the erect penis to the involved side, and occasionally causes painful erections. Frequently, this disease prevents intromission. In a later stage, the fibrotic process may extend into the corpus cavernosum, comprising tumescence distally.

Conventional treatment of Peyronie's Disease is varied and the results are somewhat unpredictable. Over a number of months, the disease may subside on a spontaneous basis. However, surgical removal of the plaque that builds up as a result of this disease can be achieved with replacement with a patch graft. However, this surgical procedure may result in further scarring and exaggeration of the defect. Another treatment is high-potency corticosteroid local injections, dexamethasone in a dose of 2-to-4 mg once or twice a week. These local injections have proven to be effective, while oral introduction of corticosteroids have not been shown to be effective. Another treatment is the use of local ultrasonic techniques, which have proved beneficial in relieving the symptoms in some cases. It is generally considered that when a plaque build-up occurred without symptoms, any treatment is unwarranted.

Another method for treating Peyronie's Disease has been disclosed in U.S. Pat. No. 4,338,300, issued July 6, 1982 to M. K. Gelbardt. The Gelbardt technique comprises the administration of an effective amount of the enzyme collagenase directly into the plaques that form in the course of the disease. However, one disadvantage to this type of treatment is that it requires a doctor's care and cannot be administered on an in-home basis. Therefore, there exists a need for an improved method for treating such a disease.

SUMMARY OF THE INVENTION

The present invention disclosed and claimed herein comprises providing an elongated tube having an inner diameter that is substantially equal to the outer diameter of an erect penis, such that the walls thereof will be adjacent the outer surface of the erect penis. A base portion is provided on the end of the elongated tube that is operable to be disposed about the base portion of an adult male penis to provide a seal therewith to air flow. The adult male penis is inserted into the end of the tube having the base portion associated therewith and the base portion moved downward against the base of the penis. A high air flow vacuum source is disposed and connected to the opposite end of the tube, such that a negative pressure is formed therein. The negative pressure results in the penis moving from a flaccid condition to an erect condition. After the penis has become erect, the seal between the base portion and the base of the penis is broken and made numerous times to create a turbulent air flow upward along the inner sides of the tube between the interior of the inner sides of the tube and the outer surface of the penis. This turbulent flow creates a significant amount of agitation within the tissue of the corpus cavernosum of the penis, as the tube is moved from side-to-side and in all directions.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
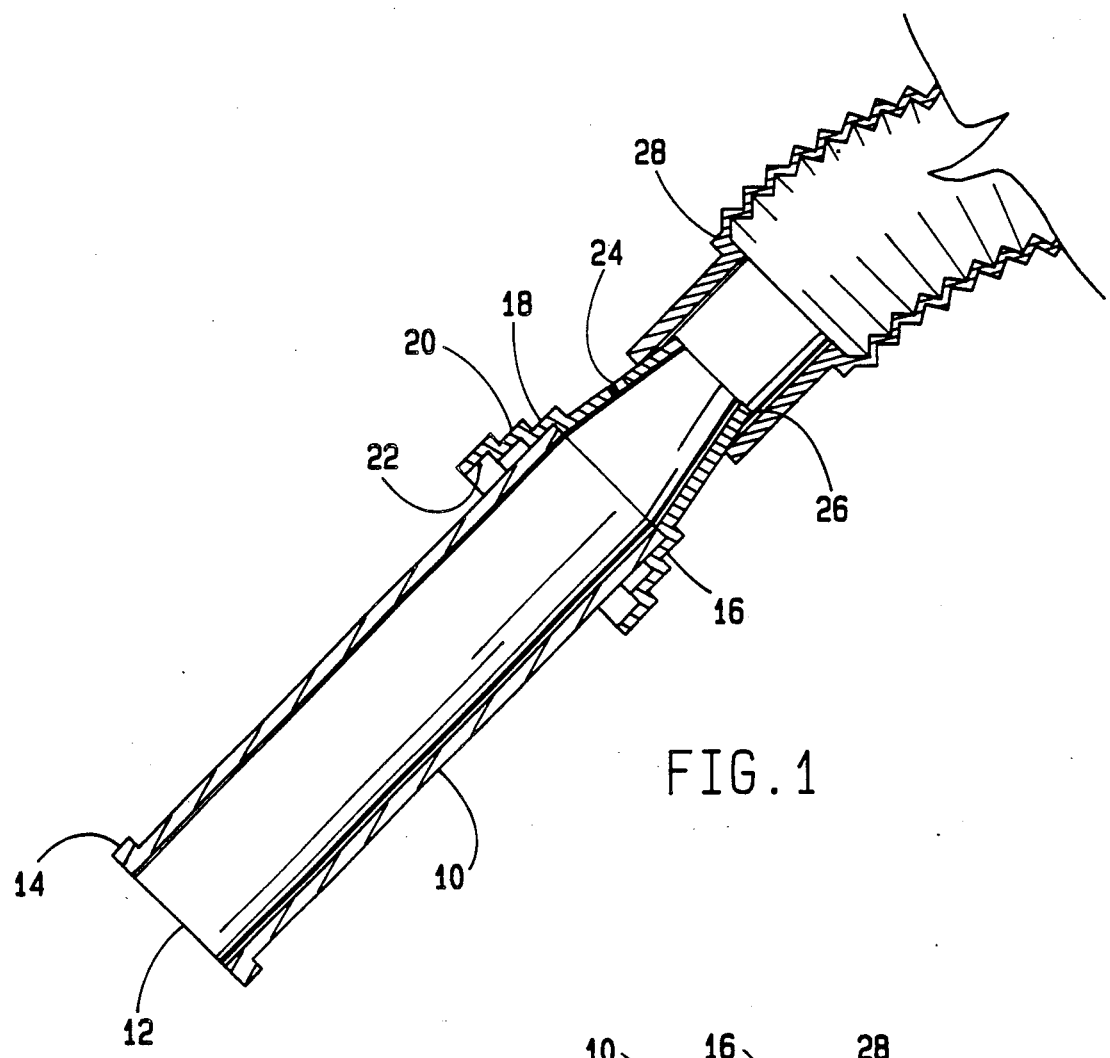
FIG. 1 illustrates a cross-sectional view of the apparatus used in the treatment of Peyronie's Disease in accordance with the present invention.

Referring now to FIG. 1, there is illustrated a cross-sectional view of the apparatus utilized in conjunction with the therapeutic treatment of the present invention. A tube 10 is provided which is fabricated from high-impact styrene with a thickness of approximately 0.25 inches with an inner diameter of 1.75 inches. The tube 10 has an opening 12 at one end thereof with a base member 14. The other end of tube 10 is inserted in a friction fit within a cap 16. The cap 16 has three cylindrical steps 18, 20 and 22, each cylindrical step having an increasingly larger diameter and connected together. The tube 10 fits into the cylindrical step 18 in a friction fit, whereas a larger diameter tube would fit within the step 20 in a friction fit and an even larger diameter tube would fit within step 22 in a friction fit. The tube that would fit in step 20 would have an inner diameter of approximately two inches and the tube that would insert in the step 22 would have an inner diameter of approximately 2.5 inches.

The cap 16 has a small orifice 24 disposed therein and an upwardly extending attachment end 26. The attachment end 26 is tapered inward and upward such that it forms a frustro-conical shape on the upper end thereof. The frustro-conical end of the portion 26 is operable to interface with a vacuum hose 28 of a conventional vacuum cleaner, as will be described hereinbelow.

The base portion 14 of the tube 10 is operable to be disposed over a flaccid penis in an adult male. When a vacuum is applied at a relatively high level by a vacuum cleaner, blood is forced into the corpus cavernosum and the penis is urged into an erect condition, wherein blood flow is enhanced to the penis.

Figure 2:
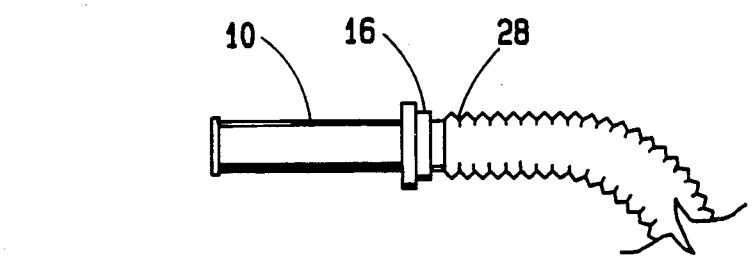
FIG. 2 illustrates an overall view of the vacuum source that is connected to the apparatus utilized in conjunction with the therapeutic method of the present invention.
Figure 2:
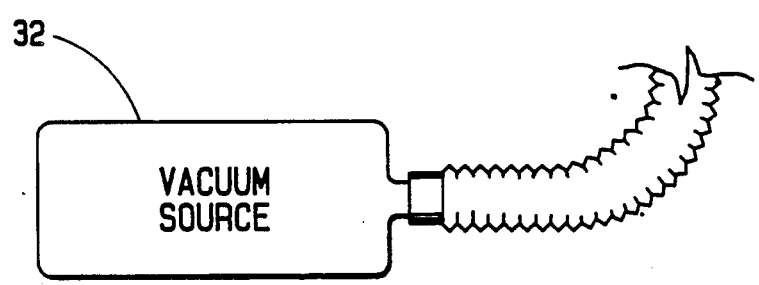

Referring now to FIG. 2, there is illustrated a detail of the vacuum source that is utilized with the apparatus for performing the therapeutic treatment of Peyronie's Disease in accordance with the present invention. The hose 28 is connected to the vacuum inlet of the vacuum source 32, which is a conventional home vacuum. This home vacuum places a significant amount of negative pressure and air flow which, as will be described hereinbelow, provides significant advantages in treating Peyronie's Disease. This air flow occurs between the outer surface of the penis and the inner surface of the tube to cause a turbulent flow and create significant agitation of the tissues of the penis.

Although systems that utilize a negative pressure tube have been disclosed in the past, it will be seen that none have provided the plaque reduction that the method of the present invention utilizes. For example, in U.S. Pat. No. 4,175,554, there is disclosed a male impotence prothesis that is alleged to be beneficial for the treatment of Peyronie's Disease. In column 7, lines 5-15, of U.S. Pat. No. 4,175,554, some note is made as to the invention thereof being utilized for treatment of Peyronie's Disease. However, this invention utilizes a relatively low pressure device that is operable to form a seal around the penis and maintain the pressure for a long duration of time, for the purpose of straightening and/or lengthening the penis. The present invention is distinguished over this due to the high vacuum source and the agitation of the penile tissue, as will be described hereinbelow.

During treatment, as described above, the penis is inserted into the tube 10 such that the base 14 provides a pseudo-seal with the base of the penis. The vacuum source is then applied such that the penis is changed from a flaccid condition to an erect condition due to blood flowing therein. The blood flowing therein is a result of the negative pressure within the tube 10 formed by the vacuum source 28. The orifice 24, which is approximately 0.25 inches in diameter is utilized to relieve some of the negative pressure and allow air to flow into the vacuum source 28 when the base 14 is securely seated at the base of the penis. However, once the negative vacuum is achieved, the tube 10 is moved from side-to-side to create a significant amount of turbulence in air flow adjacent the walls of the penis, the walls of the penis being extended outward and adjacent to the inner walls of the tube 10. The tube 10 is disposed at numerous different angles, and the base 14 pulled away from the base of the penis such that air is allowed to move inward about the base of the penis and upward adjacent the sides of the penis and into the hose 28 of the vacuum source 32. This agitation is what provides the primary therapeutic benefit, in that it is believed that the plaque build-up that exists as a result of the Peyronie's disease is believed to be broken up and dissolved through natural biological functions as a result of this severe agitation and turbulence. None of the other devices that exist in the prior art has been able to do this, due to the inability to provide such a significant vacuum source, and also the lack of turbulence provided thereby.

Applicant has tested this device in the treatment of Peyronie's Disease and has found that the course of the disease improved. Significant decrease in the deformation of the penis has resulted, which is believed to be due to the reduction of the plaques or masses of dense fibrous tissue that exists in the facia disposed about the corpus cavernosum.

Although the preferred embodiment has been described in detail, it should be understood that various changes, substitutions and alterations can be made therein without departing from the spirit and scope of the invention as defined by the appended claims.

What is claimed is:

1. A method for treatment of Peyronie's Disease comprising the steps of:
    providing an elongated tube having one open end for being inserted over the penis with a base portion that is operable to be disposed about the base of the penis, the inner diameter of the tube operable to be sufficient to contain an erect adult male penis, the tube having an opening at the opposite end for receiving a vacuum source;
    introducing the penis into the tube at the base portion thereof;
    applying a substantially high vacuum having a relatively high air flow capacity to the opposite end of the tube after the penis is inserted therein, and urging the base portion down toward the base portion of the penis;
    moving the tube after the penis has become erect such that air is allowed to pass through the space between the base portion and the base of the penis and move upward between the inner sides of the tube and the exterior surface of the penis; and
    moving the tube such that the seal between the base of the penis and the base portion of the tube is continually broken and then made again such that significant turbulence occurs about the penis in its erect condition.

2. The method of claim 1, and further comprising providing an orifice at the upper end of the tube to allow a release of negative pressure on the interior thereof.

3. The method of claim 1, wherein the step of providing the vacuum source comprises providing a vacuum source with a relatively high air flow volume.

4. The method of claim 1, and further comprising:
    providing a cap that is operable to be disposed on the end of the tube opposite the end with the base portion, the cap having provided therein a plurality of cylindrical steps, each cylindrical step increasing in diameter in a stepwise manner to receive tubes of larger and increasing diameters, the cap also having an extended outward portion for being disposed away from the tube;
    providing an opening at the opposite end of the stepwise cylindrical members to receive the vacuum;
    inserting the extended outward portion into the vacuum source; and
    inserting the end of the tube opposite the base portion into one of the cylindrical stepwise members in a friction fit.

* * * * *